US005443463A

United States Patent [19]
Stern et al.

[11] Patent Number: 5,443,463
[45] Date of Patent: Aug. 22, 1995

[54] COAGULATING FORCEPS

[75] Inventors: Roger A. Stern, Cupertino, Calif.; Richard M. Soderstrom, Seattle, Wash.; Vincent N. Sullivan; Robert L. Marion, both of San Jose, Calif.

[73] Assignee: Vesta Medical, Inc., Mountain View, Calif.

[21] Appl. No.: 106,601

[22] Filed: Aug. 16, 1993

Related U.S. Application Data

[63] Continuation-in-part of Ser. No. 877,567, May 1, 1992, Pat. No. 5,277,201, and Ser. No. 46,683, Apr. 14, 1992.

[51] Int. Cl.⁶ ............................................. A61B 17/39
[52] U.S. Cl. ............................................. 606/51; 606/52
[58] Field of Search .................. 606/41, 42, 45, 46, 606/48-52

[56] References Cited

U.S. PATENT DOCUMENTS

| 4,655,216 | 4/1987 | Tischer | 606/51 |
| 5,122,137 | 6/1992 | Lennox | 606/49 X |
| 5,190,541 | 3/1993 | Abele et al. | 606/48 X |
| 5,277,201 | 1/1994 | Stern | 606/41 |

FOREIGN PATENT DOCUMENTS 2573301  5/1986  France ................................. 606/52

OTHER PUBLICATIONS

Sugita et al., "Bipolar coagulator . . . thermocontrol", J. Neurosurg., vol. 41, Dec. 1974, pp. 777-779.

Primary Examiner—Lee S. Cohen
Attorney, Agent, or Firm—Oblon, Spivak, McClelland, Maier & Neustadt

[57] ABSTRACT

A method and an apparatus for selectively coagulating blood vessels or tissue containing blood vessels involves the placement of the blood vessels or tissue containing blood vessels between the prongs of a forceps with the jaws of the forceps containing a plurality of electrodes which are energized by radio-frequency power. A plurality of sensors are associated with the electrodes and in contact with the vessels or tissue in order to measure the temperature rise of the tissue or blood vessels and to provide a feedback to the radio-frequency power in order to control the heating to perform coagulation of the vessels or tissue. In a further development, the upper prong of the device is split into two parts with a cutting blade between the two upper parts in order to provide for cutting of the coagulated vessels subsequent to the coagulation. The cutting may be accomplished either mechanically or with an electrosurgical cutting device.

6 Claims, 5 Drawing Sheets

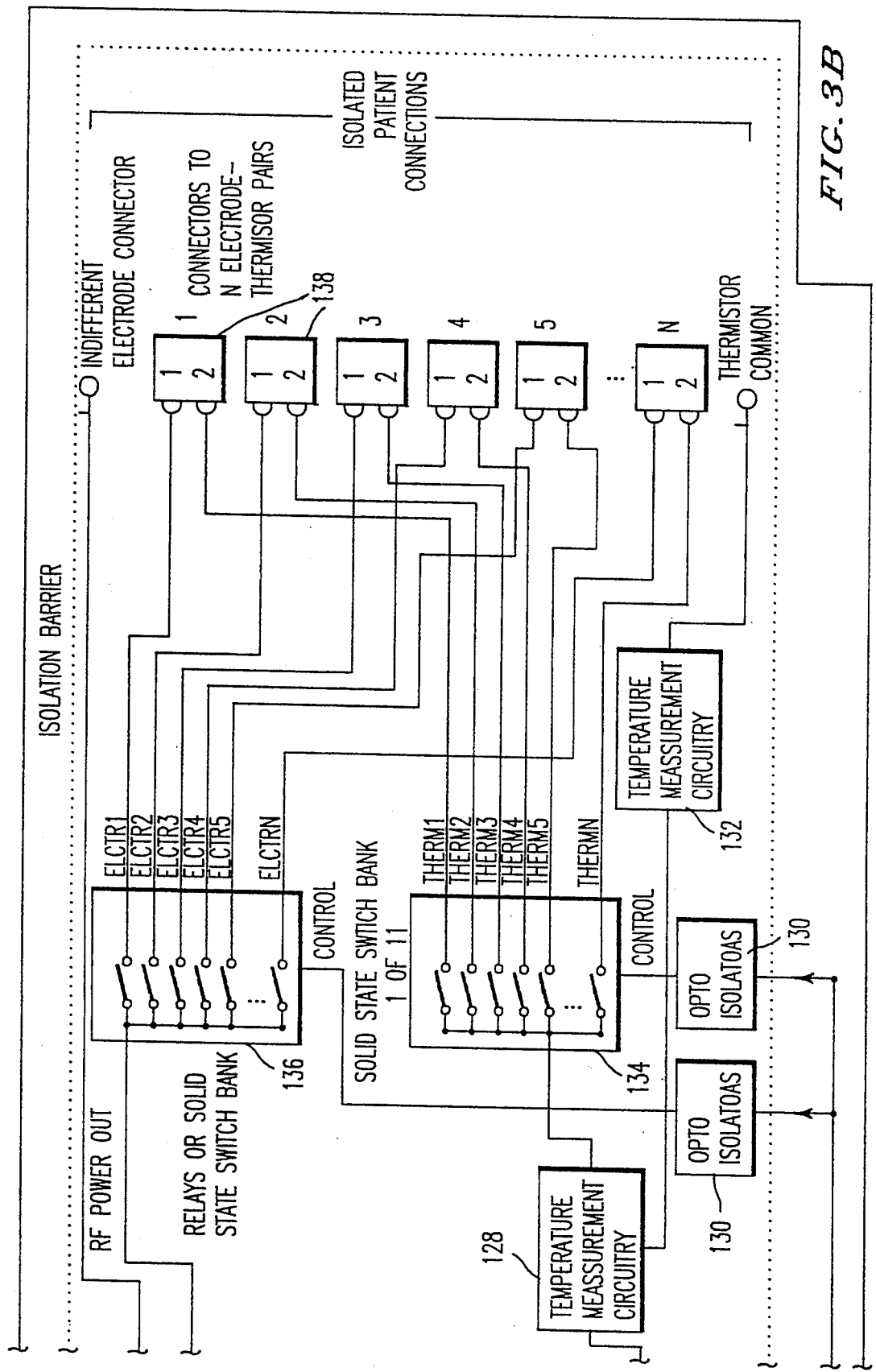

COAGULATING FORCEPS

CROSS-REFERENCE TO RELATED APPLICATIONS

This is a continuation-in-part of application Ser. No. 07/877,567, filed May 1, 1992, now U.S. Pat. No. 5,277,201 and Ser. No. 08/046,683, filed Apr. 14, 1993.

BACKGROUND OF THE INVENTION

1. Field of the Invention

The present invention relates to a method and an apparatus for an electrosurgical coagulation and cutting of regions of tissue or blood vessels over relatively large areas with temperature control.

2. Discussion of the Background

Surgical procedures and particularly electrosurgical procedures often require the complete cutoff of large regions of tissue, or the complete cutoff of the blood supply through a main artery before such surgery can be performed. A typical example is the requirement that the uterine artery be closed off before the uterus can be removed during a hysterectomy. The cutting off of the blood supply through the artery is accomplished by suture ligation, staples or clips or electrosurgical desiccation. Obviously, for large arteries, suture ligation is a difficult and long procedure which increases the time required for anesthesia resulting in an opportunity for complicating factors to arise. Aside from an increase in the length of time, there is an obvious increase in the expense of the procedure. Furthermore, when such arteries or vessels require their blood supply to be cut off during an emergency surgery, the amount of time to control the bleeding from the large vessel is more than just an expense or a complicating factor: it is a life-threatening period of time required before the actual surgery may be accomplished. Obviously, there is a need for an improved method for ligation and the cutting off of larger vessels.

Although the above example addresses the cutting off of a main artery, in many instances the blood supply needs to be cutoff to large regions of tissue containing many blood vessels and also in many instances the cutting off of the blood supply to these tissues is all that is required. In other words, in many applications, what is required is only the stopping of blood supply to a region of tissue containing many blood vessels.

In a similar manner, when cutting through large regions of tissue containing blood vessels, considerable time is expended ligating the individual blood vessels into tissue. There is a need for an improved method of cutting coagulating of such type of large regions of tissue.

One of the approaches in the electrosurgical procedure to reliably seal off large areas is the utilization of a device which can accomplish the cutoff of the blood supply through the main artery or a plurality of smaller vessels. Current electrosurgical devices face severe problems which either make their use inconvenient or severely limit their application or, in certain instances, entirely rule out the use of such electrosurgical devices. Prior art devices are inherently difficult to use over a large area or an extended linear region because it is difficult with current electrosurgical devices to produce coagulated tissue over such a large area or over such a long linear region. Furthermore, it is extremely difficult to know the degree of completion of coagulation because there is no feedback mechanism to determine when the coagulation is complete. Therefore, with the present electrosurgical devices it is entirely possible that the application of the device will have been stopped before completion of coagulation resulting in continued bleeding. It is equally possible that the device was applied for too long a time which, at best, is a waste of time and, at worst, could have caused other damage to adjacent tissue or could have burned the tissue intended to be coagulated, resulting in compromised sealing of tissue and the risk of continued bleeding.

Yet another difficulty with the present electrosurgical devices available for coagulation is the requirement for the use of multiple devices. That is, once coagulation has been completed, another device is necessary to cut the tissue.

Uniform coagulation over large areas of tissue using standard electrosurgical techniques is extremely difficult to achieve. This difficulty is due in part to the fact that it is not known how to determine the proper rate at which to apply energy or how to determine when the desired amount of coagulation has been achieved. If the energy is applied too rapidly, the superficial layers of tissue may desiccate too quickly and insulate the deeper tissues from further application of electrosurgical energy. If insufficient energy has been applied, the desired depth of penetration of the electrosurgical energy may never be achieved. The only feedback currently available to an operator of the prior art electrosurgical devices is the visible inspection of the surface of the tissue which is being coagulated or monitoring of the level of RF current. Surface inspection is no indication of any effect achieved in deeper layers of tissue. Similarly, a drop in RF current does not differentiate between the formation of an insulating superficial layer as complete desiccation. Thus, the application of electrosurgical procedures to cut off blood supply is a developed skill based upon experience which either requires separate training in this field or a stop-and-inspect procedure with even such procedure failing when the energy is applied too quickly because the deeper tissues may have become insulated from further heat application.

There thus exists a long-felt need for a rapid, efficient, safe and sure method and device for completely cutting off the blood supply through an artery for vessel and the subsequent cutting of the artery or vessel in order to prepare for a further surgical procedure.

A similar need exists for an efficient, safe and sure method and device for sealing or coagulating large areas of vascular tissue such as mesentery, bowel, mesoappendix, lung, fat tissue, lymph nodes, fallopian tubes, pedicles and the like.

SUMMARY OF THE INVENTION

Accordingly, one object of the present invention is to provide a novel apparatus and method for performing safe and rapid blood supply cutoff through an artery, a vessel, or other tissue in an efficient and sure manner without the need for visual inspection.

It is a further object of the present invention to provide a generic line of electrosurgical tools capable of supplying temperature-controlled electrosurgical energy over large areas.

It is also an object of the present invention to provide a single device which allows for both stoppage of blood supply and the cutting of the artery itself subsequent to stoppage of the blood supply.

These and other objects are accomplished by using a plurality of area electrodes and the individually controlling the energy delivered to each electrode by means of a switchable temperature feedback circuit.

It is a further object to provide a feedback means for monitoring temperature, impedance and power to provide a control algorithm for operation of the device.

The objects of the present invention are provided by way of a forceps including split jaws and having a plurality of electrodes as well as a plurality of temperature sensors wherein operation of the device is accomplished by a scissors-like movement of the forceps.

It is a further object of the present invention to provide a structure whereby the split jaws of the coagulating forceps have an intermediate cutting blade combined with said forceps in order to sever the ligated vessel in the center of a coagulated area.

It is a further object of the present invention to provide a coagulating forceps with electrosurgical generation energy applied through a switching circuit.

It is a further object of the present invention to provide bipolar delivery of energy to the coagulating forceps.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1A:
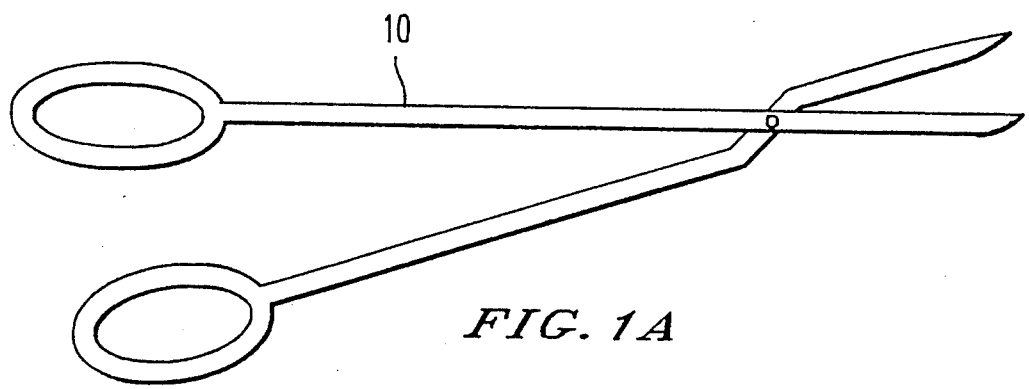
FIGS. 1A and 1B show a general view of a coagulating forceps according to the present invention, with FIG. 1B showing a close-up view of a compressed vessel being clamped by the forceps.
Figure 1B:
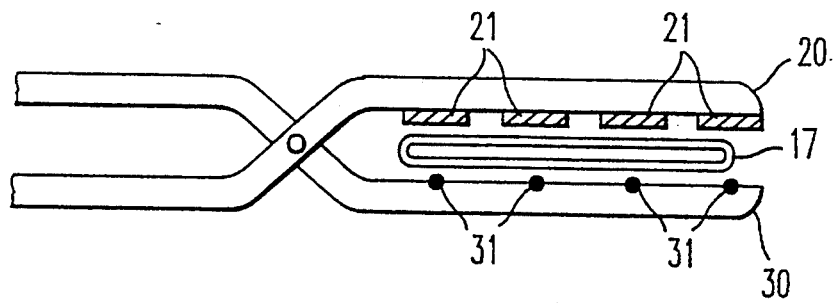

Referring now to the drawings, wherein like reference numerals designate identical or corresponding parts throughout the several views, and more particularly to FIGS. 1A and 1B thereof, there is illustrated a coagulating forceps in accordance with the present invention.

FIG. 1A and FIG. 1B show that the forceps 10 having handles 11 and 12 forming a scissor-like arrangement by which the jaws 20 and 30 are brought into contact with the compressed vessel or tissue 17 as shown in FIG. 1B. A plurality of electrodes 21 are shown on the upper jaw and a plurality of sensors 31 on the lower jaw. Although four electrodes 21 and four temperature sensors 31 are illustrated, any number and any arrangement or size of electrodes may be used depending upon the type of vessel or artery, vessel or other tissue which is to be cut off. That is, for different types of operations and for different types of arteries, vessels, or other tissues, different devices or forceps may be configured to conform with certain areas of the human body or certain access areas which are used in normal surgical procedures may be utilized. As an example, the forceps may be extended to form a needle-nose configuration or the size of the forceps may be reduced and accordingly the shape of the electrodes may be changed to take into account the size of the forceps. Furthermore, the configuration of the scissors-like arrangement is for purposes of illustration and the jaws may take the form of a clamping structure having either a straight head or an angled head as is normally used in any of a variety of clamping devices used for surgical procedures. Additionally, the scissors-like structure may be replaced with any other mechanism that will cause the forceps jaws to be brought together when activated. In particular, various types of mechanisms typically used in devices for laparoscopic surgery would be available.

When the forceps of FIG. 1 are used, a two-step procedure is involved in order to cut the vessel. That is, first the forceps 10 are clamped across the vessel as shown in FIG. 1B and the tissue is heated for a predetermined period at a predetermined temperature in order to ensure the coagulation of the vessel. Then, the forceps is removed and a cutting device such as a knife or an electrosurgical cutting is used. This requirement of two devices in the two-step operation can be eliminated by the single device of FIG. 2B.

Figure 2A:
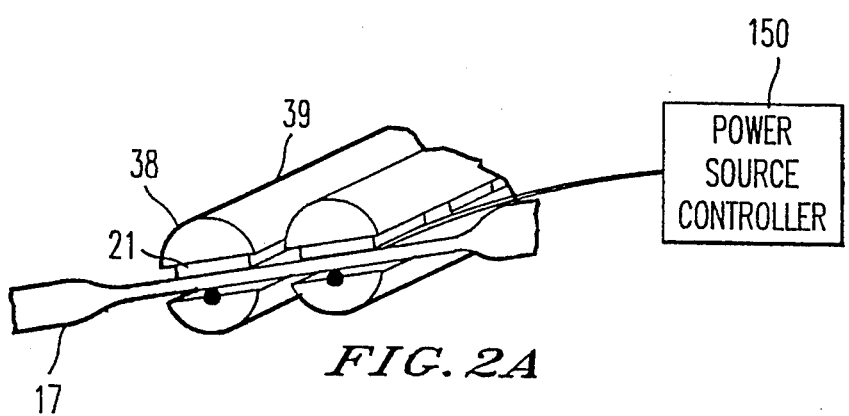
FIGS. 2A, 2B and 2C show a construction variation with FIG. 2A illustrating the clamping of a vessel by a forceps having split upper and lower jaws, FIG. 2B showing the addition of a cutting blade to a split upper jaw and FIG. 2C illustrating a side position cutting blade for a single pair of upper and lower jaws.
Figure 2B:
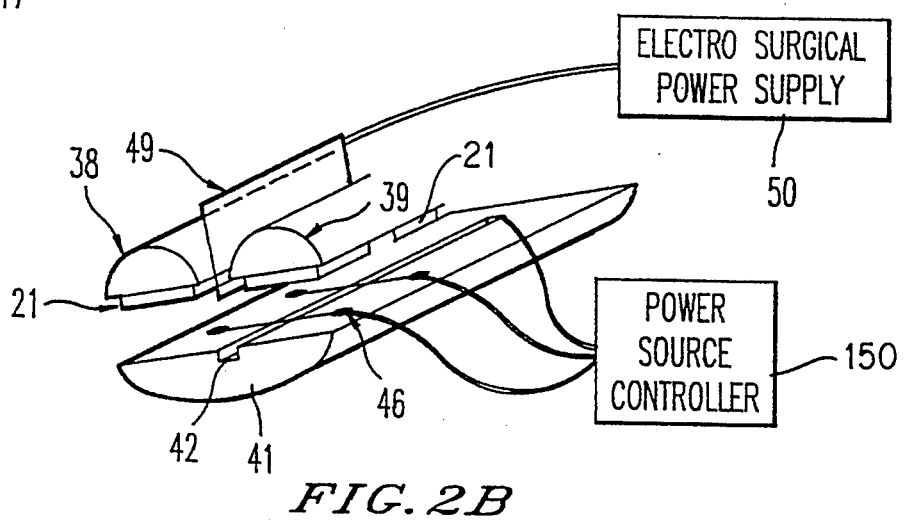

The FIGS. 2A and 2B illustrate a bifurcated top jaw with the electrodes 21 on the top jaw being divided between each of the two parts 38 and 39 of the top jaw. The bottom jaw 41 is a flat surface having a groove 42. The bottom surface contains the sensors 46 identical to the sensors 31 in FIG. 1B. Also shown in the FIG. 2B is a cutting blade 49 schematically shown as attached to an electrosurgical unit power generator 50 of the type generally used for electrosurgical cutting procedure.

Figure 2C:
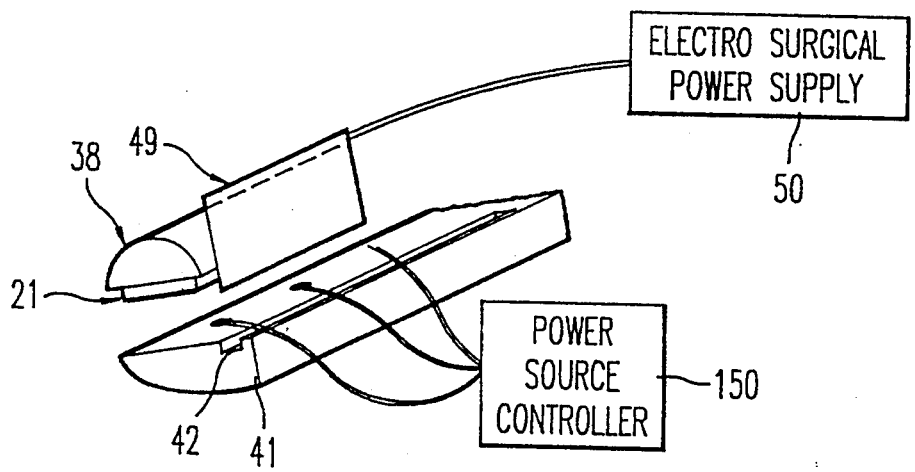

With the arrangement of FIG. 2B, the multi-segmented electrodes are powered and the tissue is heated by the power source controller 150 until the compressed vessel is coagulated and then the cutting blade 49, which slides between the upper jaws 38 and 39, cuts through the tissue into the lower groove 42. With the embodiment of FIG. 2B showing the connection of the cutting blade to the electrosurgical power unit 50, such cutting can occur by way of a normal electrosurgical action which involves a cutting by an arc between the blade and the bottom of the groove 42 of the lower jaw 41. Electrosurgical cutting requires less mechanical force and more completely assures the cutting of the tissue. Thus, a two-step operation is carried out using the same apparatus with the first step of the heating and coagulation of the tissue taking place separate from the actual cutting of the tissue. The cutting of the tissue is completely independent of the operation of the multi-segmented electrodes which have already accomplished the coagulation. When the cutting takes place, the power is no longer supplied to the multisegmented electrodes. Subsequently, the cutting blade either directly by mechanical force or through the action of an electrosurgical cutting accomplishes the actual cutting through of the tissue whose blood supply has been cut off by the prior coagulation. Essentially, this amounts to stopping blood flow on two sides of an area and then the subsequent cutting in the middle of the area with the stopping of blood flow and the cutting is accomplished by a single device. The FIG. 2C illustrates a side blade cutting structure with a single pair of upper and lower jaws 38 and 41. The lower groove 42 still retains the cutting blade 49 after passing through the tissue in a manner similar to FIG. 2B. The cutting action of the blade 49 can also be accomplished by an electro-surgical action in a manner similar to previously described operation of the cutting blade of FIG. 2B. The exception to the operation of the instrument of FIG. 2B is that the device of FIG. 2C has a cutoff of blood supply or a coagulation on only one side of the area to be cut. Side cutting would be accomplished by the operation of the device of FIG. 2C is useful in particularized areas of surgery which either do not require cutoff of blood supply on both sides of the tissue to be cut or require or prefer continued blood supply flow adjacent to one side of the cut area.

Figure 3A:
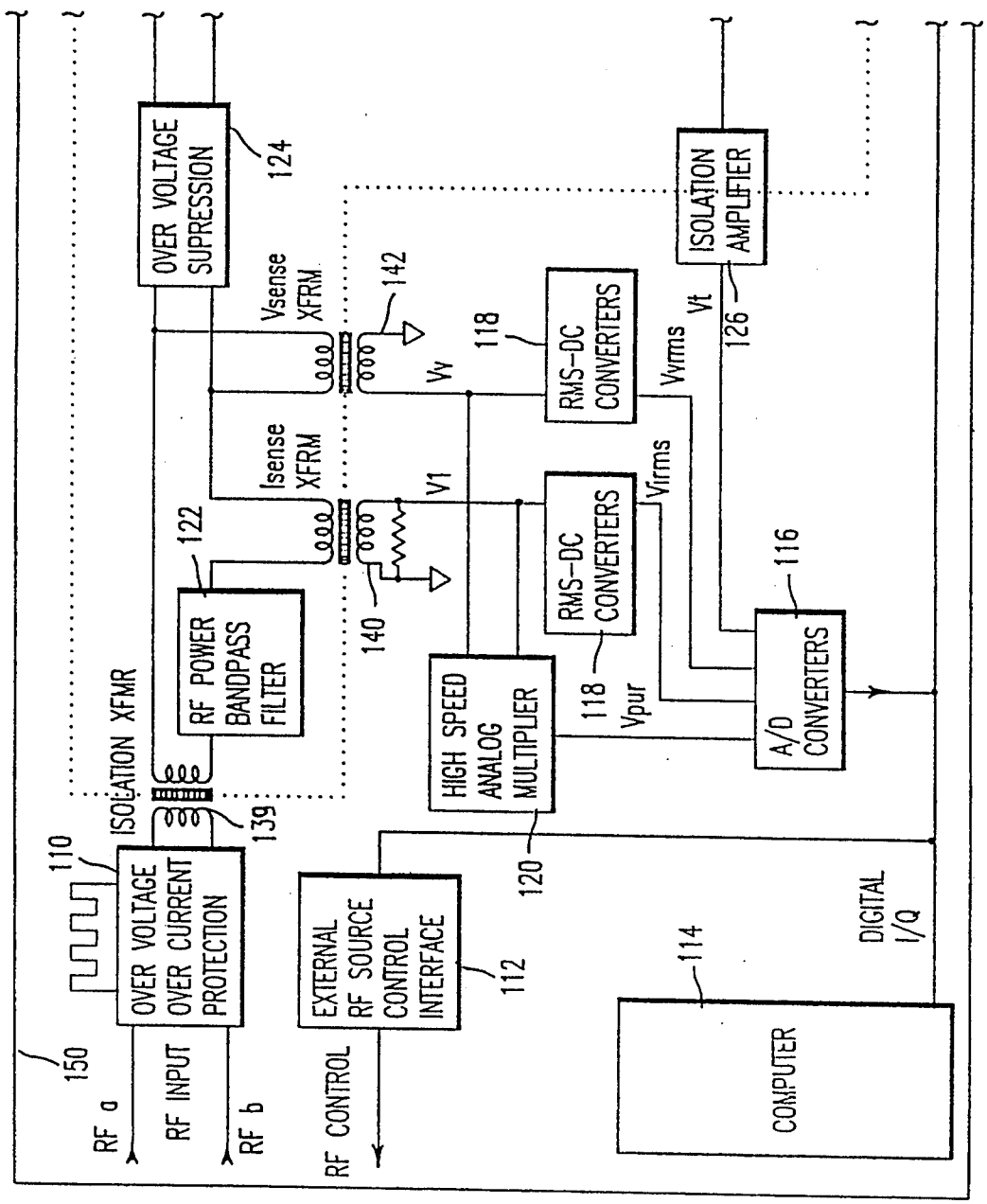
FIG. 3 illustrates a schematic structure for a power source controller system.

The FIG. 3 is a schematic representation of the power source controller 150 of FIGS. 2A and 2B and the switch matrix for the multi-segmented forceps discussed in conjunction with either FIG. 1 or FIG. 2. The electrical leads connect to the electrode-thermistor pairs of the forceps by way of connectors 138. The thermistor leads of the thermistors 31 (46) are connected to the matrix switchbank 134 and the electrode leads of electrodes 21 are connected to the switchbank 136. Each thermistor 31 (46) is sampled by means of a temperature measurement circuit 128 and the isolation amplifier 126 before being converted to digital form in the converter 116 and fed to the computer 114. The temperature measurement circuitry compares the measured temperature with a thermistor reference voltage 132. The electrode switch 136 is controlled in response to the output of the computer 114 by means of the opto-isolators 130. Input power from the RF input passes through the overvoltage and overcurrent protector 110 and is filtered by the bandpass filter 122 before being subjected to overvoltage suppression by the suppression unit 124. The voltage is isolated by means of transformers 139, 140 and 142 with the transformer voltages $V_i$ and $V_v$ from the transformers 142 and 144 being converted by the RMS-DC converters 118 into an RMS voltage to be fed to the converters 116. Prior to conversion, the signals $V_i$ and $V_v$ are also fed to the high-speed analog multiplier 120. RF control from computer 114 is provided through interface 112.

Figure 4:
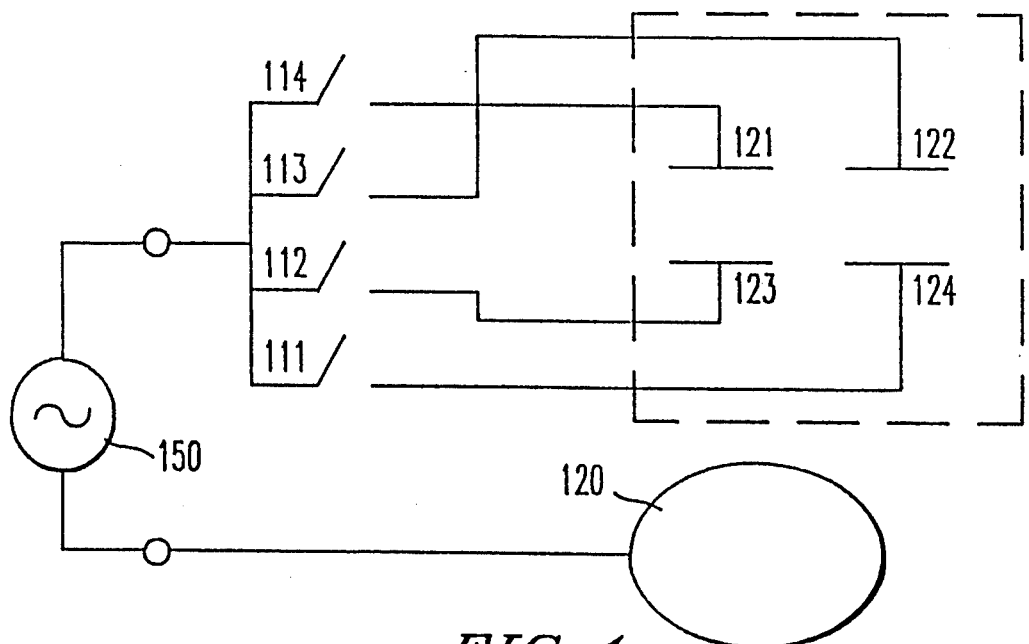
FIG. 4 is an illustration of a schematic of a monopolar construction of the power delivery system.

The FIG. 4 provides a schematic representation of the connection of power source controller 150 of FIG. 3 to a multi-segmented electrode forceps having an illustrated four electrodes. The illustrated embodiment of FIG. 4 shows a monopolar construction having a connection to a patient ground pad 120. The electrodes 121–124 may correspond to the electrodes 21 in FIG. 1b and may be located on the upper jaw 20 in line or they may be located as shown in FIG. 2 with two of the electrodes being on one of the upper split jaws 38 and the other two being on the upper split jaw 39. Although four electrodes are shown in the FIG. 4, there is no limit based upon the principles of operation. Neither is there a limit on the arrangement of a particular number of electrodes on a particular portion of the jaw. The nature of the surgery to be performed and particularly the nature of the device for performing such surgery will provide the impetus for the size of the electrodes and the number of electrodes and the positioning of the electrodes on the forceps.

In the illustration of FIG. 4, there is a voltage from the controlled power source being fed to one or more of the electrodes 121–124 depending on the condition of the switches 111–114. This is a monopolar operation and the grounding occurs by way of the patient ground pad 120. The temperature sensors 31 are not shown in the FIG. 4 embodiment for purposes of simplification but would be clearly positioned in a manner similar to FIG. 1 and FIG. 2 and the outputs would be fed to the device of FIG. 3.

Any large tissue area or vessel which needs to be coagulated can be covered by a number of electrodes by segmenting the large area into a number of smaller area electrodes of the type 121–124. With this type of structure of smaller area electrodes, individual control of the energy to each electrode through the switching circuit of FIG. 4 is available in order to achieve controlled coagulation over a large area of tissue. The temperature sensors 31 or 46 are employed to sense the tissue temperature. Allowing the tissue temperature to reach a desired value and maintaining that temperature at that level for an appropriate period of time provides the physician with feedback concerning the coagulation process which would be impossible to achieve with a visible inspection of the surface tissue of the vessel being coagulated. This temperature feedback ideally provides for the control of the depth of the treatment and uses what is known as a "slow cook" of the tissue over a period of anywhere from several seconds to several minutes to achieve the desired therapeutic affect of cutting off the blood flow.

Studies of thermotolerance of cells indicate that maintaining cells at 43° C. for one hour produce a cell death. The time required is halved for each degree centigrade increase above 43° C. Cell death occurs because cellular enzymes necessary to support metabolism are destroyed.

Figure 5:
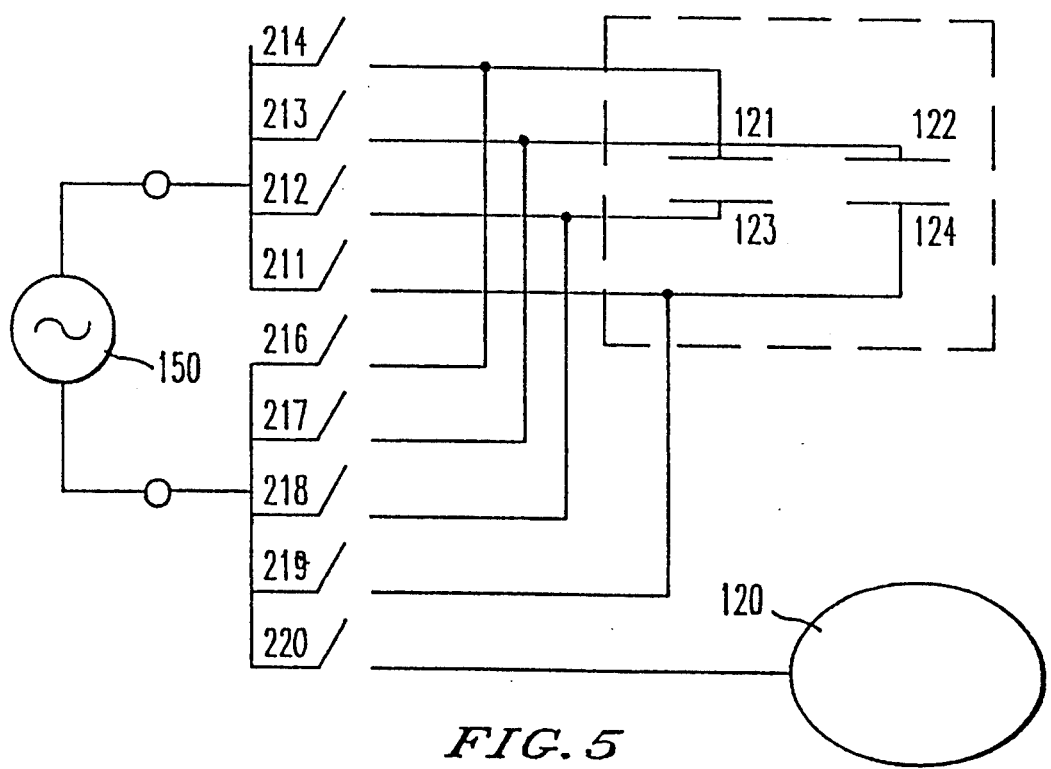
FIG. 5 is a schematic of a bipolar/monopolar construction of the power delivery system.

The multi-electrodes/temperature feedback concept for coagulating large areas or linear regions can be improved with respect to the delivery of energy to particular points by way of the switching arrangement of FIG. 5 which provides for the ability to use either a monopolar operation or a bipolar operation. FIG. 5 utilizes the same four electrodes 121–124 and a similar voltage source 150 with the same patient ground pad 120 as used in FIG. 4. The essence of the FIG. 5 monopolar/bipolar switching arrangement is that the physician or operator has the ability to provide either monopolar or bipolar operation. When switch 220 is closed and the switches 216–219 remain open, the device functions essentially the same as the FIG. 4 embodiment. That is, it provides monopolar operation. On the other hand, if the switch 220 is opened and if pairs of switches, with one of the pair being selected from the switch 211 to 214 and the other being selected from 216 to 219, are operated in proper conjunction, the electrodes 121–124 will provide a bipolar operation. As an example, if switch 214 is closed as well as switch 218, then the current will pass from electrode 121 to electrode 123. In a similar manner, if switch 213 is closed as well as switch 219, there will be a bipolar operation with current flowing between electrode 122 and 124. Bipolar operation is not limited to these 121–123 and 122–124 pair couplings because if switch 214 and switch 217 are closed there will be bipolar operation between the electrodes 121 and 122 with current passing from 121 to 122.

The embodiment of FIG. 5 not only provides a choice between monopolar and bipolar operation but also provides a flexibility within the bipolar operation so that any two or any combination of pairs of electrodes 121–124 may be utilized together. Obviously, if switch 214 were thrown in conjunction with switch 216, nothing would occur because there would be a short. The operation in a bipolar mode provides the additional flexibility whereby some of the electrodes may be positioned on the top half and the bottom half respectively of the jaws of the forceps 10. That is, instead of the forceps having the electrodes positioned in line on the top jaw 20 as shown in FIG. 1, they may be positioned with two electrodes 121–122 on a top jaw and electrodes 123 and 124 on the bottom jaw. Of course, the same remains true with respect to any number of electrodes other than the four shown in the embodiment of FIGS. 4 and 5.

Figure 6:
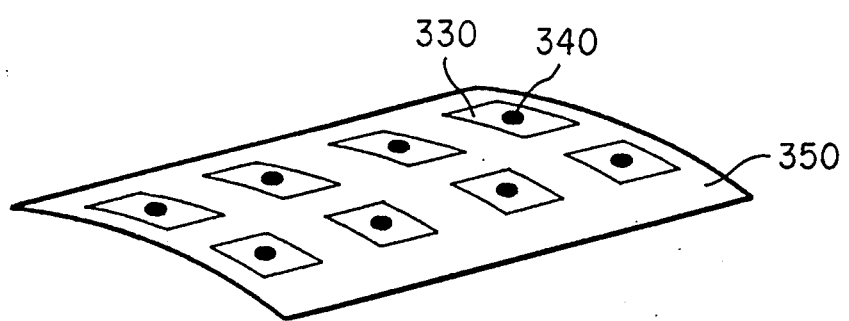
FIG. 6 is a coagulating linear patch.

The FIG. 6 illustrates an embodiment utilizing the electrode arrangement concept and the temperature sensor feedback concept to provide effectively a patch which may be used to control or stop surface bleeding. The patch contains multiple electrodes 330 and an associated temperature sensor 340 with the size of the patch 350 being dependent upon physiologic considerations and desired area of coverage. The same is true with respect to the choice of the number of sensors and the number of associated electrodes. The feedback mechanism control by way of the FIG. 3 power source would function in the same manner except that a physician would control the operation of the feedback mechanism to provide temperatures which would correspond to the requirements of the injury on the surface of the person receiving this patch. Although the operation would be dependent upon the type of injury or the type of surface to be controlled with respect to blood flow, it provides a slow cooking process at a stabilized and controlled temperature so that all areas underneath the patch 350 may be treated in a uniform manner without "hot spots" which would cause either injury or undesirable and uneven control of bleeding while also unnecessarily cauterizing tissue.

The use of a coagulating forceps provides uniform coagulation over large areas of tissue by providing the proper application of energy to provide the desired depth of penetration without reliance on a visible inspection of the surface of the tissue or vessel being coagulated. The ability to segment the large area electrosurgical electrode into a number of smaller area electrodes and individually controlling the energy to each electrode through the multiplexing circuit of either FIG. 4 or 5 provides a degree of flexibility beyond the state of the art as well as a degree of assurance heretofore unknown. Thus use of many small electrodes is generally preferable to a single large electrode. The advantage of many small electrodes is better control such as the ability to cause tissue to reach a therapeutic temperature with a small amount of power.

The temperature sensors provide the feedback mechanism which allows the tissue temperature to reach a desired value and be maintained at that level for an appropriate period of time. This provides necessary information concerning the coagulation process which would otherwise be unavailable to the physician. The monitoring of the tissue impedance and the actual delivered power provide the ability to control the coagulation precisely. Once this coagulation is controlled to the satisfaction of the physician and the coagulating job has been completed, the cutting mechanism, either by way of electrosurgical cutting or manual cutting, severs the ligated vessel in the center of the coagulated area as shown in the embodiment of FIG. 2. Any number of sets of electrodes can be utilized depending upon the area and the location of the area to be coagulated and the head of the forceps can be angled or otherwise maneuvered using many of the same physiologic considerations provided for the selection of any surgical tool subject to electrical connection to the power generation source and the number of wires and space required for such connection.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. An implement for selectively coagulating blood vessels or tissues containing blood vessels, comprising:
   at least two opposable members and a means for permitting movement of said at least two opposable members toward and away from each other;
   electroconductive electrode means positioned on at least one of said at least two opposable members for effecting electrical contact with said vessels to be coagulated, said electroconductive electrode means includes a plurality of electrically isolated separate electrodes positioned on at least one of said at least two opposable members; and
   radio frequency power means connected to said electrodes for selectively delivering radio-frequency energy to each electrode to pass current through and coagulate said vessels positioned between said at least two opposable members, 2. The implement according to claim 1, further including a switching means for providing individual control of energy to each of said electrically isolated separate electrodes.

3. The implement according to claim 2, wherein said switching means includes means for selecting at least one of monopolar and bipolar energy to be delivered to each of said electrically isolated separate electrodes.

4. The implement according to claim 3, wherein said switching means includes means for providing bipolar energy to said electrodes.

5. The implement according to claim 1, and further including temperature sensing means positioned on at least one of said at least two opposable members for measuring the temperature of said vessels in close proximity to said electrodes.

6. The implement according to claim 1, wherein electroconductive electrode means are positioned on both opposable members.

* * * * *

UNITED STATES PATENT AND TRADEMARK OFFICE
CERTIFICATE OF CORRECTION

PATENT NO. : 5,443,463

DATED : August 22, 1995

INVENTOR(S) : Roger A. Stern, et. al.

It is certified that error appears in the above-indentified patent and that said Letters Patent is hereby corrected as shown below:

Title page, item [63], under Related U.S. Application Data: "April 14, 1992" should read--April 14, 1993--.

Signed and Sealed this

Twenty-first Day of November, 1995

Attest:

BRUCE LEHMAN

Attesting Officer

Commissioner of Patents and Trademarks